United States Patent [19]

Dajani et al.

[11] 3,996,214
[45] Dec. 7, 1976

[54] 5-(1,1-DIPHENYL-4-(CYCLIC AMINO) BUT-2-TRANS-EN-1-YL)-2-ALKYL-1,3,4-OXADIAZOLES AND INTERMEDIATES THERETO

[75] Inventors: Esam Z. Dajani, Buffalo Grove; Chung H. Yen, Skokie, both of Ill.

[73] Assignee: G. D. Searle & Co., Chicago, Ill.

[22] Filed: Feb. 23, 1976

[21] Appl. No.: 660,206

[52] U.S. Cl. .................. 260/240 R; 260/307 G; 260/308 D
[51] Int. Cl.² ............. C07D 413/06; C07D 221/20; C07D 401/00
[58] Field of Search .................. 260/240 R, 307 G

[56] References Cited

UNITED STATES PATENTS

| 3,847,923 | 11/1974 | Kreider | 260/240 R X |
| 3,862,173 | 1/1975 | Carr et al. | 260/240 R |
| 3,917,615 | 11/1975 | Adelstein | 260/307 G X |

OTHER PUBLICATIONS

B568,405, Mar. 1976, Adelstein et al., 260/307 G.

*Primary Examiner*—Allen B. Curtis
*Attorney, Agent, or Firm*—Joy A. Serauskas

[57] ABSTRACT

This invention encompasses novel 5-[1,1-diphenyl-4-(cyclic amino)but-2-trans-en-1-yl]-2-alkyl-1,3,4-oxadiazoles and intermediates thereto. These compounds are useful anti-diarrheal agents.

4 Claims, No Drawings

5-(1,1-DIPHENYL-4-(CYCLIC AMINO) BUT-2-TRANS-EN-1-YL)-2-ALKYL-1,3,4-OXADIAZOLES AND INTERMEDIATES THERETO

The present invention is concerned with 5-[1,1-diphenyl-4-(cyclic amino)but-2-trans-en-1-yl]-2-alkyl-1,3,4-oxadiazoles and intermediates thereto. More particularly, this invention is concerned with compounds of the formula

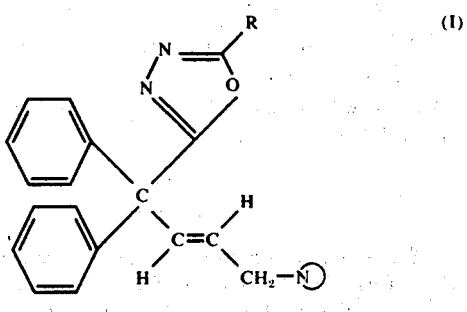

wherein R is lower alkyl containing from 1 to 6 carbon atoms;

Ⓝ is a cyclic secondary amine residue selected from the group consisting of azabicycloalkyl containing 6 to 9 carbon atoms and having at least 5 atoms in each ring, pyrrolidino, piperidino, and hexamethylenimino; and the stereochemical configuration of the double bond is trans; and intermediates thereto.

Particulary preferred compounds of this invention are those of the formula

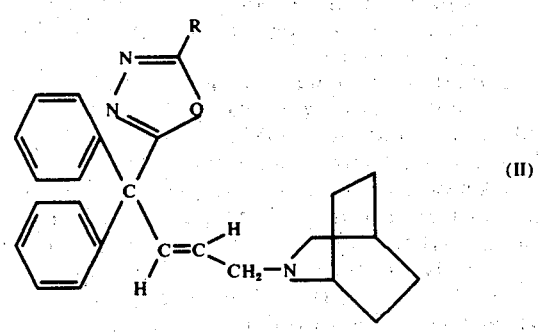

wherein R is lower alkyl containing 1 to 6 carbon atoms and the double bond is in the trans configuration.

The lower alkyl groups referred to hereinbefore contain 1 to 6 carbon atoms and are exemplified by methyl, ethyl, propyl, butyl, pentyl, hexyl and the corresponding branched-chain isomers thereof.

The cyclic secondary amine residues which are azabicycloalkyl groups containing 6 to 9 carbon atoms and having at least 5 atoms in each ring are exemplified by groups such as 7-azabicyclo[2.2.1]hept-7-yl, 2-azabicyclo[2.2.2]oct-2-yl, 2-azabicyclo[3.2.1]oct-2-yl, 3-azabicyclo[3.2.1]oct-3-yl, 6-azabicyclo[3.2.1]oct-6-yl, 3-azabicyclo[3.2.2]non-3-yl, 8-azabicyclo[4.3.0]non-8-yl, 2-azabicyclo3.2.2]non-2-yl, 2-azabicyclo[3.3.1]non-2-yl, 3-azabicyclo[3.3.1]non-3-yl, 2-azabicyclo[4.3.0]non-3-yl, 7-azabicyclo[4.3.0]non-7-yl, 8-azabicyclo[4.3.1]dec-8-yl, 2-azabicyclo[4.4.0]dec-2-yl, and 7-azabicyclo[4.2.2]dec-7-yl.

Equivalent to the compounds of formulas (I) and (II) for the purposes of this invention are the pharmaceutically acceptable acid addition salts thereof. Such acid addition salts can be derived from a variety of inorganic and organic acids such as sulfuric, phosphoric, hydrochloric, hydrobromic, hydroiodic, sulfamic, citric, lactic, pyruvic, oxalic, maleic, succinic, tartaric, cinnamic, acetic, benzoic, salicylic, gluconic, ascorbic and related acids.

The compounds of the present invention are useful in consequence of their valuable pharmacological properties. They are, for example, anti-diarrheal agents as evidenced by their ability to inhibit gastrointestinal motility as set out in the following tests.

CHARCOAL MEAL TEST

The method used for this assay is a modification of the techniques previously described by Macht and Barba-Gose, J. Amer. Pharm. Ass., 20, 558(1931), and Janssen and Jageneau, J. Pharm. Pharmacol., 9, 381(1957). Details are as follows:

A group of six, male Charles River mice weighing 20–25 g. which have been previously fasted for 24 hours are pretreated with the test compounds administered orally as a solution in water or suspended in 0.5% methyl cellulose. A constant volume of 10 ml./kg. is employed. Thirty minutes following administration of the test compounds, the animals are given a single oral dose of charcoal which consists of 0.2ml. per mouse of 10% charcoal suspended in 1.0% methyl cellulose. Three and a half hours after charcoal administration, the animals are sacrificed and the cecum examined for the absence or presence of charcoal on an all-or-none basis.

The median effective dose ($ED_{50}$) is then calculated for each compound using the logistic method of Berkson (1953).

CASTOR OIL-INDUCED DIARRHEA IN THE RAT

Adult Charles River male rats are fasted in community cages for 24 hours prior to the test, with free access to water. The test compound is then administered intragastrically (suspended in 0.5% methyl cellulose) one hour prior to the intragastric administration of a dose of 1.0 ml. castor oil per rat. The rats are then observed for the presence or absence of diarrhea at hourly intervals for up to 8 hours past the castor oil administration. Using the method of Berkson (1953), the median effective dose ($ED_{50}$) values are calculated at each hourly interval for the test compound.

In addition to their anti-diarrheal activity, the compounds of this invention demonstrate little or no analgesic activity at the test doses. The assessment of this activity is conducted by the following assay:

TAIL CLIP TEST

A special clip is applied to the base of the tail of an adult male mouse weighing 18–25 grams and the time for the animal to turn around to bite at the clip is measured. The sensitivity of each mouse is determined one-half hour prior to drug administration and only those mice attempting to bite the clip are included in the experiment. The test compound is then administered either intragastrically or intraperitoneally and the response to placement of the clip is determined at 30, 60, 90 and 120 minutes after treatment. A response is considered positive if the animal takes more than 2 times the pre-drug time to bite at the clip at any of these time intervals. A test compound is considered active when 50 percent or more of the animals used show a positive response.

A representative compound of this invention which is particularly active in the above Charcoal Meal Test anti-diarrheal assay is 5-[1,1-diphenyl-4-(2-azabicyclo[2.2.2]oct-2-yl)but-2-trans-en-1-yl]-2-methyl-1,3,4-oxadiazole. This compound also exhibits no analgesic effects at a dose of 100 mg./kg. administered orally.

The compounds of formula (I) may be combined with various pharmaceutical carriers to provide compositions suitable for use in the treatment of diarrhea. The dosage of these compounds is dependent upon various factors, such as the compound employed and the particular response obtained. Typical dosages for use as an anti-diarrheal agent vary from 0.1 to 25 mg./kg. per day administered orally.

The compounds of the present invention are conveniently prepared by the reaction sequence set out in Scheme A.

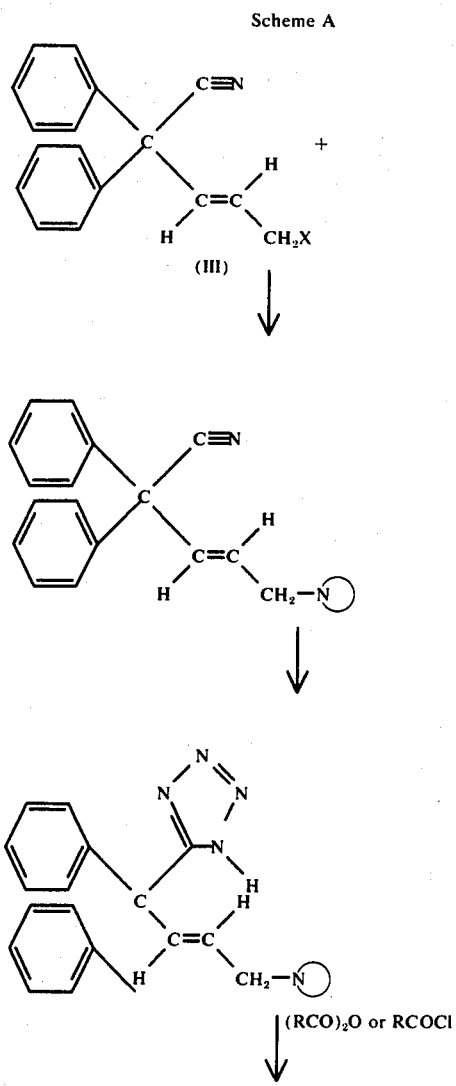

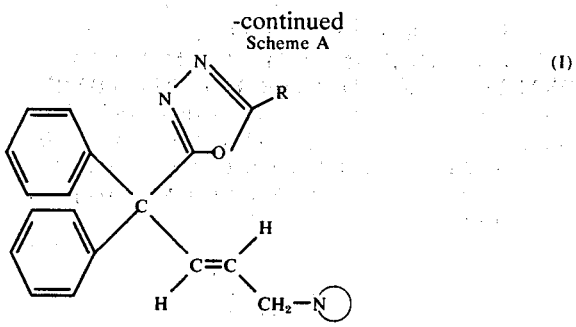

As shown in Scheme A, the secondary amine of formula (IV) wherein

is defined as hereinbefore is reacted with an alkyl halide of formula (III) wherein the X represents an iodo, bromo or chloro atom, to form the nitrile of formula (V). Depending on the nature of the reactants, it is possible to carry out this reaction in the presence or absence of a solvent. The use of a solvent is, however, generally preferred. Suitable solvents include, but are not limited to, carbon tetrachloride, ethanol, methanol and methyl isobutyl ketone. Time and temperature are not critical factors for the conduct of this reaction, typical temperatures varying from room temperature to reflux, and typical times being in the range of 2–48 hours.

The novel nitrile intermediates of formula (V) are additionally useful as anti-diarrheal agents which possess little or no analgesic effects. A representative compound, 2,2-diphenyl-5-(2-azabicyclo[2.2.2]oct-2-yl)-3-trans-pentenenitrile is active in the Charcoal Meal Test and shows no analgesic effects at a dose of 100 mg./kg. administered orally.

The nitrile of formula (V) is then reacted with an azide ion by methods similar to those described by Moersch and Morrow, J. Med. Chem., 10, 149 (1967) to obtain the tetrazole of formula (VI).

The tetrazoles of formula (VI) are converted to the compounds of formula (I) by reaction with an appropriate acylating agent of formula (VII) wherein R is defined as hereinbefore. This reaction is conveniently conducted in an organic solvent, a particularly preferred solvent being pyridine.

The starting material of formula (III) is conveniently generated by the reaction of 2,2-diphenyl-3-trans-pentenenitrile with an appropriate allylic halogenating agent. A particularly preferred method of generating this starting material involves the reaction of the aforementioned 2,2-di-phenyl-3-trans-pentenenitrile with N-bromosuccinimide. This reaction is usually conducted in an inert organic solvent, a particularly preferred solvent being carbon tetrachloride. The use of free-radical initiators such as infrared light and a peroxide, i.e., benzoyl peroxide, in such a reaction is desirable.

The following examples describe in detail compounds illustrative of the present invention and methods which have been devised for their preparation. It will be apparent to those skilled in the art that many modifications, both of materials and methods, may be practiced without departing from the purpose and intent of this disclosure. Throughout the examples hereinafter set forth, temperatures are given in degrees Centigrade (° C.) and relative amounts in parts by weight, except as otherwise noted.

EXAMPLE 1

A solution of 10.0 parts of 2,2-diphenyl-4-bromopentanenitrile in 47 parts pyrrolidine is heated to reflux for 17 hours under a nitrogen atmosphere. Then, the solution is cooled, and stripped in vacuo to leave a brown oil which is partitioned between ethyl ether and dilute hydrochloric acid. The ether phase is separated, washed with dilute sodium bicarbonate, dried over anhydrous sodium sulfate, and stripped in vacuo. The residual liquid is then distilled to afford, as a colorless liquid, 2,2-diphenyl-3-trans-pentenenitrile, boiling at about 115°–123° C. at 0.1 mm pressure. This compound is represented by the following structural formula.

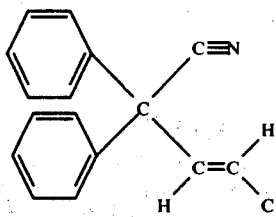

EXAMPLE 2

A solution of 5.25 parts 2,2-diphenyl-3-trans-pentenenitrile, 4.2 parts N-bromosuccinimide, and a catalytic amount of benzoyl peroxide in 80 parts carbon tetrachloride is heated under the irradiation of an infrared lamp for 4.5 hours. After cooling to 20° C., the mixture is filtered and the solid washed with 16 parts carbon tetrachloride. The filtrate and carbon tetrachloride washing are combined, thus affording a solution of 2,2-diphenyl-5-bromo-3-trans-pentenenitrile in carbon tetrachloride. This compound is represented by the following structural formula.

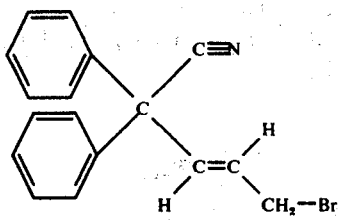

EXAMPLE 3

To a warm solution of 7.54 parts of 2-azabicyclo[2.2.2]-octane hydrochloride in 28 parts ethanol is added a solution of 2.04 parts sodium hydroxide in 32 parts ethanol. The resulting solid precipitate is filtered and to the filtrate is added a carbon tetrachloride solution containing about 8 parts 2,2-diphenyl-5-bromo-3-trans-pentenenitrile. After standing at room temperature for about 48 hours, the solution is stripped in vacuo and the residue partitioned between dilute sodium hydroxide and ether. The ethereal layer is separated and extracted with 5% acetic acid and water. The aqueous extracts are then combined and strongly basified with aqueous sodium hydroxide to liberate an oil which is extracted into ether. The ether solution is dried over anhydrous sodium sulfate and stripped in vacuo to afford an oil. The oil is purified by dissolving it in 8 parts acetone and diluting the solution with 200 parts water. The solid which precipitates is filtered and recrystallized from n-hexane to afford 2,2-diphenyl-5-(2-azabicyclo[2.2.2]oct-2-yl)-3-trans-pentenenitrile as white prisms. This compound melts at about 65°–66.5° C. and is represented by the following structural formula.

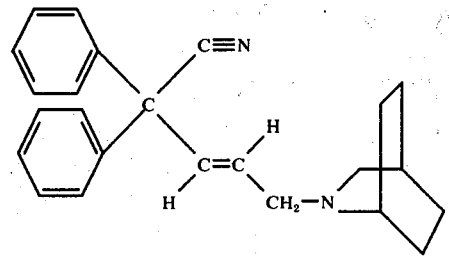

EXAMPLE 4

A mixture of 3.03 parts 2,2-diphenyl-5-(2-azabicyclo[2.2.2]oct-2-yl)-3-trans-pentenenitrile, 1.15 parts sodium azide, 0.95 parts ammonium chloride, 0.02 part lithium chloride and 22 parts N,N-dimethylformamide is heated with stirring at 88° C. for 18 hours under a nitrogen atmosphere. After cooling, the reaction mixture is stripped under high vacuum to afford a residue which is partitioned between dilute potassium hydroxide and ether. The dilute potassium hydroxide layer is separated, the pH adjusted to about 6.5–7.0 with aqueous hydrochloric acid and extracted several times with portions of methylene chloride. The methylene chloride extracts are combined, dried over anhydrous sodium sulfate and stripped in vacuo to afford, as a yellow solid, 5-[1,1-diphenyl-4-(2-azabicyclo[2.2.2]oct-2-yl)-but-2-trans-en-1-yl]-1H-tetrazole. This compound melts at about 250°–254° C. with gas evolution and is represented by the following structural formula.

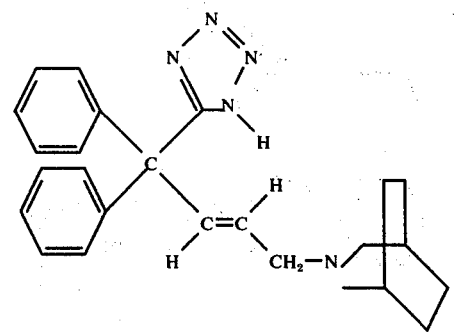

EXAMPLE 5

A solution of 0.41 part 5-[1,1-diphenyl-4-(2-azabicyclo[2.2.2]oct-2-yl)but-2-trans-en-1-yl]-1H-tetrazole and 0.9 part acetic anhydride in 4 parts dry pyridine is heated to reflux under nitrogen for 1 hour. After cooling, the reaction mixture is stripped in vacuo. The residue is suspended in dilute potassium hydroxide and extracted with ether. The ethereal extract is separated, washed with water, dried over anhydrous sodium sulfate and stripped in vacuo. Recrystallization from ethyl ether affords, as tan plates, 5-[1,1-diphenyl-4-(2-azabicyclo[2.2.2]oct-2-trans-en-1-yl]-2-methyl-1,3,4-oxadiazole. This compound melts at about 132°–134.5° C. and is represented by the following structural formula.

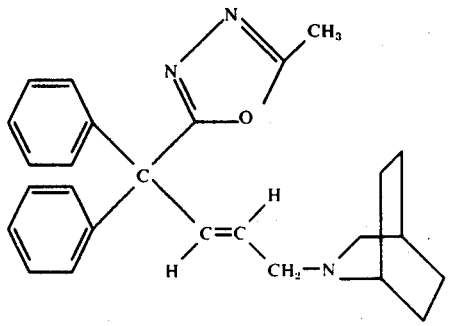

EXAMPLE 6

Substitution of an equivalent quantity of piperidine hydrochloride in the procedure of Example 3 affords 2,2-diphenyl-5-piperidino-3-trans-pentenenitrile.

EXAMPLE 7

When an equivalent quantity of 2,2-diphenyl-5-piperidino-3-trans-pentenenitrile is substituted in the procedure of Example 4, there is obtained 5-(1,1-diphenyl-4-piperidino-but-2-trans-en-1-yl)-1H-tetrazole.

EXAMPLE 8

Repetition of the procedure of Example 5 using an equivalent quantity of 5-(1,1-diphenyl-4-piperidinobut-2-trans-en-1-yl)-1H-tetrazole affords 5-(1,1-diphenyl-4piperidinobut-2-trans-en-1-yl)-2-methyl-1,3,4-oxadiazole. This compound is represented by the following structural formula.

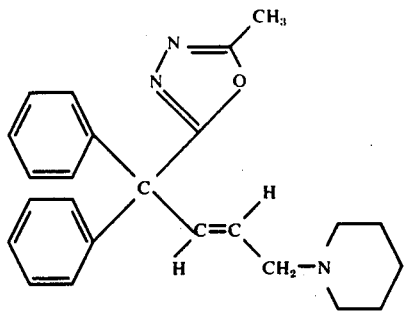

EXAMPLE 9

Substitution of an equivalent quantity of pyrrolidine hydrochloride in the procedure of Example 3 affords 2,2-diphenyl-5-pyrrolidino-3-trans-pentenenitrile.

EXAMPLE 10

When an equivalent quantity of 2,2-diphenyl-5-pyrrolidino-3-trans-pentenenitrile is substituted in the procedure of Example 4, there is obtained 5-(1,1-diphenyl-4-pyrrolidinobut-2-trans-en-1-yl)-1H-tetrazole.

EXAMPLE 11

Repetition of the procedure of Example 5 using an equivalent quantity of 5-(1,1-diphenyl-4-pyrrolidinobut-2-trans-en-1-yl)-1H-tetrazole affords 5-(1,1-diphenyl-4-pyrrolidinobut-2-trans-en-1-yl)-2-methyl-1,3,4-oxadiazole. This compound is represented by the following structural formula.

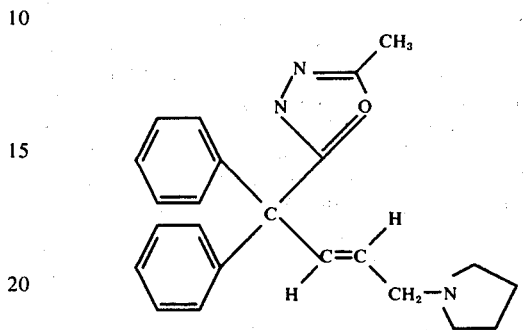

EXAMPLE 12

Substitution of an equivalent quantity of 3-azabicyclo[3.2.2]nonane hydrochloride in the procedure of Example 3 affords 2,2-diphenyl-5-(3-azabicyclo[3.2.2]non-3-yl)-3-trans-pentenenitrile.

EXAMPLE 13

When an equivalent quantity of 2,2-diphenyl-5-(3-azabicyclo[3.2.2]non-3-yl)-3-trans-pentenenitrile is substituted in the procedure of Example 4, there is obtained 5-(1,1-diphenyl-4-[(3-azabicyclo[3.2.2]non-3-yl)but-2-trans-en-1-yl]-1H-tetrazole.

EXAMPLE 14

Repetition of the procedure of Example 5 using an equivalent quantity of 5-(1,1-diphenyl-4-[(3-azabicyclo[3.2.2]-non-3-yl)but-2-trans-en-1-yl]-1H-tetrazole affords 5-(1,1-diphenyl-4-[(3-azabicyclo[3.2.2]non-3-yl)but-2-trans-en-1-yl]-2-methyl-1,3,4-oxadiazole. This compound is represented by the following structural formula.

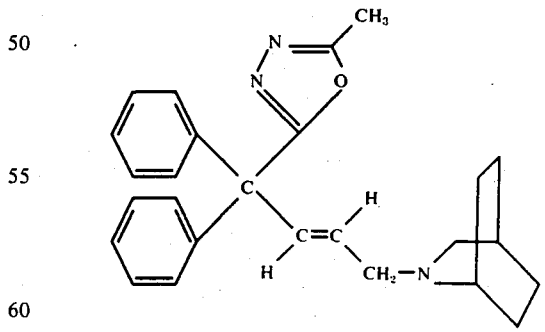

EXAMPLE 15

Substitution of an equivalent quantity of 7-azabicyclo[2.2.1]heptane hydrochloride in the procedure of Example 3 affords 2,2-diphenyl-5-(7-azabicyclo[2.2.1]hept-7-yl)-3-trans-pentenenitrile.

EXAMPLE 16

When an equivalent quantity of 2,2-diphenyl-5-(7-azabicyclo[2.2.1]hept-7-yl)-3-trans-pentenenitrile is substituted in the procedure of Example 4, there is obtained 5-(1,1-diphenyl-4-[(7-azabicyclo[2.2.1]hept-7-yl)but-2-trans-en-1-yl]-1H-tetrazole.

EXAMPLE 17

Repetition of the procedure of Example 5 using an equivalent quantity of 5-(1,1-diphenyl-4-[(7-azabicyclo[2.2.1]-hept-7-yl)but-2-trans-en-1-yl]-1H-tetrazole and propionic anhydride in place of the acetic anhydride affords 5-(1,1-diphenyl-4-[(7-azabicyclo[2.2.1]hept-7-yl)but-2-trans-en-1-yl]-2-ethyl-1,3,4-oxadiazole. This compound is represented by the following structural formula.

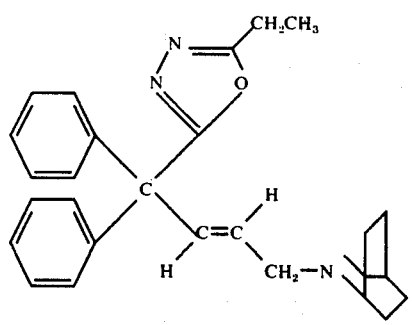

What is claimed is:

1. A compound of the formula

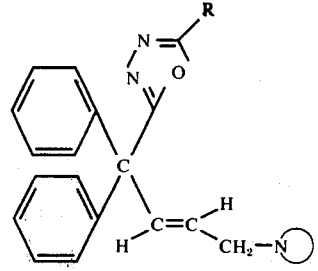

wherein R is a lower alkyl containing from 1 to 6 carbon atoms:

◯ is a cyclic secondary amine residue selected from the group consisting of azabicycloalkyl containing 6 to 9 carbon atoms and having at least 5 atoms in each ring pyrrolidino, piperidino, and hexamethylenimino; and the stereochemical configuration of the double bond is trans.

2. A compound according to claim 1 of the formula

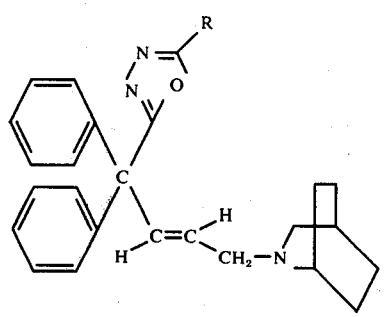

wherein R is lower alkyl containing from 1 to 6 carbon atoms and the double bond is in the trans configuration.

3. The compound according to claim 1 which is 5-[1,1-diphenyl-4-(2-azabicyclo[2.2.2]oct-2-yl)but-2-trans-en-1-yl]-2-methyl-1,3,4-oxadiazole.

4. The compound which is 2,2-diphenyl-5-(2-azabicyclo[2.2.2]oct-2-yl)-3-trans-pentenenitrile.

* * * * *